United States Patent
Rogers et al.

(10) Patent No.: US 8,094,320 B2
(45) Date of Patent: Jan. 10, 2012

(54) EN-FACE OCT WITH PARALLEL DETECTOR ARRAY

(75) Inventors: John A. Rogers, Canterbury (GB); Mark Hathaway, Canterbury (GB)

(73) Assignee: Optos Plc (GB)

( * ) Notice: Subject to any disclaimer, the term of this patent is extended or adjusted under 35 U.S.C. 154(b) by 719 days.

(21) Appl. No.: 12/092,503

(22) PCT Filed: Oct. 31, 2006

(86) PCT No.: PCT/CA2006/001781
§ 371 (c)(1),
(2), (4) Date: Oct. 7, 2008

(87) PCT Pub. No.: WO2007/051292
PCT Pub. Date: May 10, 2007

(65) Prior Publication Data
US 2009/0153874 A1    Jun. 18, 2009

(30) Foreign Application Priority Data
Nov. 2, 2005   (GB) .................................. 0522340.9

(51) Int. Cl.
*G01B 11/02* (2006.01)
(52) U.S. Cl. ....................................................... 356/497
(58) Field of Classification Search .................. 356/479, 356/497
See application file for complete search history.

(56) References Cited

U.S. PATENT DOCUMENTS

| | | | |
|---|---|---|---|
| 6,141,577 A | 10/2000 | Rolland et al. | |
| 6,485,413 B1 | 11/2002 | Boppart et al. | |
| 7,394,549 B2 * | 7/2008 | Hendriks et al. | 356/497 |
| 2003/0020922 A1 | 1/2003 | Crowley et al. | |
| 2004/0239943 A1 | 12/2004 | Izatt et al. | |
| 2005/0140982 A1 | 6/2005 | Chen et al. | |
| 2005/0171438 A1 | 8/2005 | Chen et al. | |

FOREIGN PATENT DOCUMENTS
DE        19929406 A1    12/2000
(Continued)

OTHER PUBLICATIONS

Hauger, Christoph et al, "High speed low coherence interferometer for optical coherence tomography," Coherence Dmain Optical Methods in Biomedical Science and Clinical Applications VI, Proceedings of SPIE, 2002, pp. 1-9, vol. 4619, SPIE.

*Primary Examiner* — Tarifur Chowdhury
*Assistant Examiner* — Jonathan Hansen
(74) *Attorney, Agent, or Firm* — Laubscher & Laubscher, PC

(57) ABSTRACT

In an OCT apparatus, an object light beam is returned from a target and interferes with a reference light beam. Image information is obtained from a depth Z in the target that depends on the optical path difference between the object and reference beams with a resolution that depends on the coherence length of the light. A scanner transversely scans the target with the object beam over a plurality of image points defined by the resolution of the apparatus. Interface optics directs the reference and object beams onto an array of detector elements such that the optical path difference between the reference beam and the object beam varies across the array. The reference beam and the object beam interfere with each other over the array of detector elements for individual image points on the target during each transverse scan. A memory stores a subset of data points corresponding to each individual image point obtained from each detector elements of the array. A processor processes one or more of the subsets of data points to derive image information extending over a range of depths in the target for each individual image point. The obtained image information is displayed on a displace device.

16 Claims, 2 Drawing Sheets

FOREIGN PATENT DOCUMENTS

| | | |
|---|---|---|
| GB | 2406638 A | 4/2005 |
| JP | 2001255264 | 9/2001 |
| WO | 9835203 A2 | 8/1998 |
| WO | WO 03/062802 | 7/2003 |
| WO | 2004055570 A2 | 7/2004 |
| WO | 2005060823 A1 | 7/2005 |

* cited by examiner

EN-FACE OCT WITH PARALLEL DETECTOR ARRAY

FIELD OF THE INVENTION

This invention relates to the field of optical coherence tomography (OCT), and in particular to a method and apparatus for obtaining OCT image information from en-face scans of a target, such as the retina of an eye.

BACKGROUND OF THE INVENTION

OCT is a technique wherein imaging information can be obtained in the depth or z-direction of a sample, typically the retina of the eye. In one type of OCT, the retina is scanned with an object beam from an interferometer having a broadband light source with a short coherence length. A signal is obtained from the returned beam at depth positions wherein the optical path difference is less than the coherence length, which is typically in the order of a few microns. By adjusting the path length in the reference beam, it is possible to adjust the depth position within the target, which is assumed to be partially transparent, from which imaging information is obtained. In order to obtain a useful signal, as is known in the art, some form of modulation must be applied to the object beam.

Different scanning techniques may be employed as described, for example, in U.S. Pat. No. 5,975,697, the contents of which are herein incorporated by reference. In the so-called A scan, the sample is scanned along a single axis in the depth direction to generate a reflectivity profile along the Z axis at a particular point in the X-Y plane. In a B scan, the sample is also scanned in either the X or Y direction so as to generate a horizontal or vertical slice extending into the sample. The B-scan results from a succession of A scans. In en-face scanning, with which the present invention is concerned, image slices in the X-Y plane are taken at different depths to build up a composite three-dimensional image of the object. This is achieved by varying the optical path difference between the reference beam and object beam in the interferometer. A displaceable mirror is placed in the reference beam to vary the path length of the reference beam and thereby the optical path difference.

In a conventional OCT arrangement, the returned light from the object beam is mixed with the reference beam in a coupler and passed through a splitter to a differential photodetector arrangement. As the object beam scans across the target in the X-direction in a raster fashion, the instantaneous signal at the output of the photodetector arrangement is a function of the reflectivity of the target at each pixel at the current coordinate position determined by the scanner and at a depth determined by the optical path difference, which in turn is set by a displaceable mirror in the path of the reference beam. At the end of each frame, corresponding to a complete raster scan, the position of the mirror is adjusted to change the depth position, i.e. the position on the Z axis from where image information is obtained, and a new raster scan is performed at the new depth position determined by the position of the displaceable mirror. Multiple frames have to be taken in order to build up a three dimensional image of the target, or in the case of a single section image, multiple scans are required. The prior art in effect processes the signal pixel by pixel in a serial fashion. This is a slow and cumbersome process.

SUMMARY OF THE INVENTION

In accordance with the present invention the reference beam and object beam are combined in such a way that a complete a data corresponding to a range of depths is captured simultaneously for each X-Y position of the object beam on the object. This is achieved by using an array of detector elements, overlapping the reference and returned object beams on the array, and capturing a set of data in parallel for each X-Y position of the object beam. The different optical path lengths for the two beams to the different detector elements results in each detector element producing image information at a different depth.

Accordingly one aspect of the invention provides a method of generating three-dimensional images in an OCT apparatus, wherein an object light beam is returned from target and interferes with a reference light beam, and wherein image information is obtained from a depth Z in the target that depends on the optical path difference between the object and reference beams with a resolution that depends on the coherence length of the light, comprising: transversely scanning the target with the object beam over a plurality of image points defined by the resolution of the apparatus; at individual image points on the target during each transverse scan, causing the reference beam and the object beam to interfere over an array of detector elements such that the optical path difference between the reference beam and the object beam varies across the array; for each said individual image point storing a subset of data points obtained from each detector element of the array; and processing one or more of said subsets of data points to derive image information extending over a range of depths in the target for each said individual image point.

It will be appreciated that the invention relates to what is referred to as "en face" scanning, that is scanning where the image plane is considered to be the X-Y plane, and a series of sectional images are taken in the X-Y plane at different positions in the Z-direction, i.e. the depth direction. The scanning is referred to as transverse because the image is scanned, typically with a galvo-scanner, in a raster fashion in the X-Y plane. It will however be appreciated that the orientation in the X-Y plane is immaterial. For example, in theory the raster scan could occur in the Y direction or in any other orientation relative to the target.

The invention permits the depth information at each image point for each image point in the Z-direction to be obtained simultaneously. The resolution of the image points in the Z direction is determined by the spacing of the detector elements on the detector array as well as the coherence length of the light used. The resolution of the image points in the transverse direction is determined by timing. An image point is created each time a subset of data points is captured from the array of detector elements.

Unlike the prior art, only a single raster scan need be performed to build up a complete three dimensional image since owing to the processing of the array of detector elements in parallel, each scan contains image information for a set of image points in the X-Y plane, as well as sets of image points in the Z-direction. A single raster scan thus permits the construction of a three-dimensional image of the target.

The invention further provides an OCT apparatus, wherein an object light beam is returned from target and interferes with a reference light beam, and wherein image information is obtained from a depth Z in the target that depends on the optical path difference between the object and reference beams with a resolution that depends on the coherence length of the light, comprising a scanner for transversely scanning the target with the object beam over a plurality of image points defined by the resolution of the apparatus; an array of detector elements; interface optics for directing the reference and object beams onto the array of detector elements such that the optical path difference between the reference beam and the object beam varies across the array, whereby the reference beam and the object beam interfere with each other over said array of detector elements for individual image points on the target during each transverse scan; a memory for storing a subset of data points corresponding to each said individual image point and obtained from each detector element of the array; and a processor for processing one or more of said subsets of data points to derive image information extending over a range of depths in the target for each said individual image point; and a display device for displaying said image information.

The invention still further provides a detector for an OCT apparatus, wherein an object light beam is returned from target and interferes with a reference light beam, and wherein image information is obtained from a depth Z in the target that depends on the optical path difference between the object and reference beams with a resolution that depends on the coherence length of the light, comprising an array of detector elements; a first input for receiving an optical fiber carrying a reference beam; a second input for receiving an optical fiber carrying an object beam; and interface optics for directing said reference beam and said object beam onto said array in an overlapping fashion such that they interfere with each other on said array, the optical path difference between said reference beam and said object beam varying across said array.

BRIEF DESCRIPTION OF THE DRAWINGS

The invention will now be described in more detail, by way of example, only with reference to the accompanying drawings, in which.

DETAILED DESCRIPTION OF THE PREFERRED EMBODIMENTS

Figure 1:
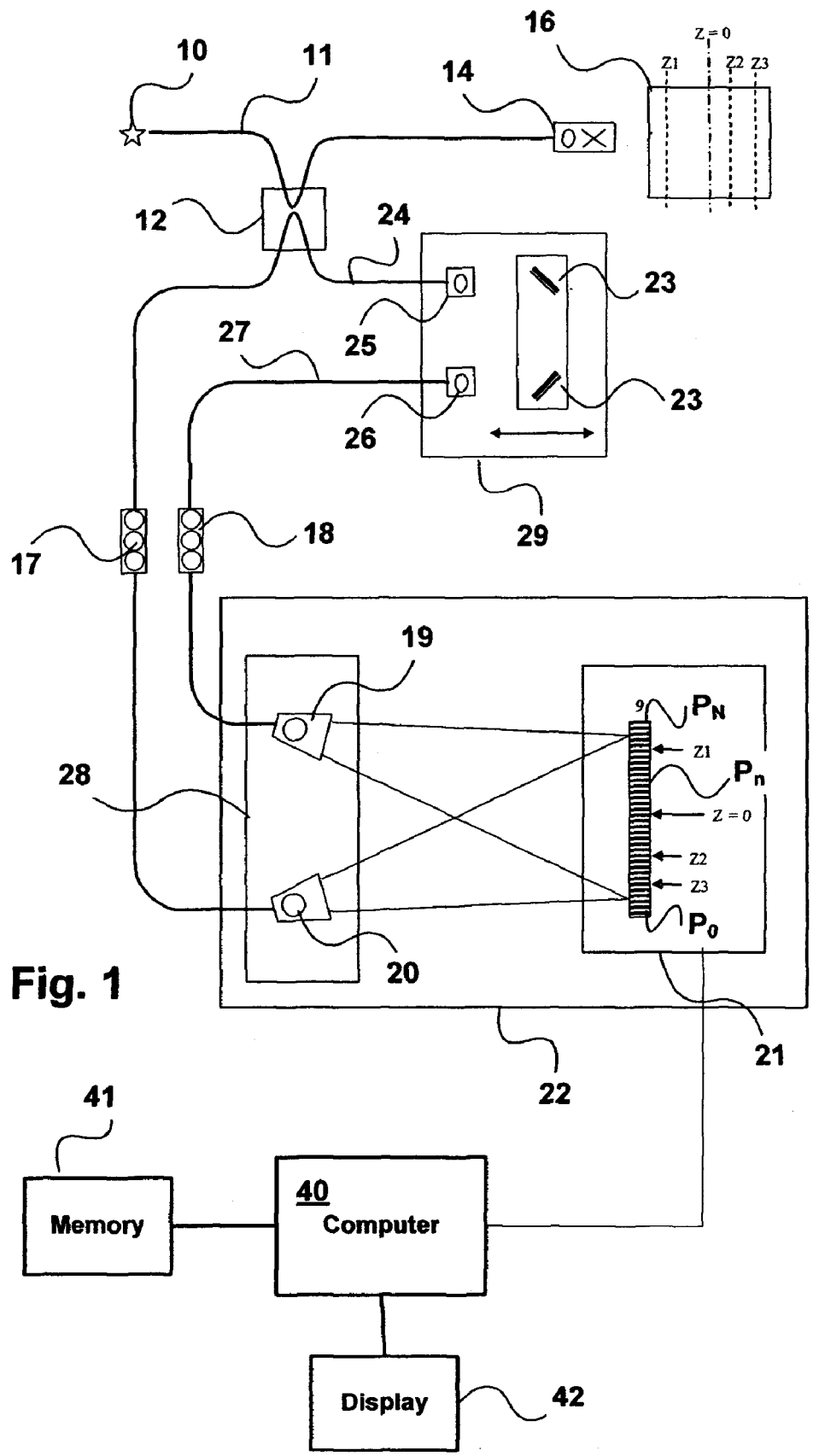
FIG. 1 is a schematic diagram of an OCT apparatus with parallel en-face scanning.

An apparatus for performing parallel en-face OCT scanning in accordance with the invention will be described with reference to FIG. 1. In FIG. 1, a broadband source generates a light beam that is directed, in this embodiment, into an optical fiber 11 and through a beam splitter/coupler 12 to a scanning head 14 comprising interface and scanning optics. Typically, the interface and scanning optics include a galvo scanner for performing an en-face raster scan of the target, which may be the retina of an eye.

Although this embodiment is described using optical fibers, it will be understood that it can also be implemented in bulk optics. The principles are the same.

The object beam is directed from the interface optics 14 onto the target 16, which is scanned in a raster fashion in the X-Y plane (en-face scanning). The return object beam is then passed back through splitter/coupler 12, through polarization controller 17 to detector unit 22, which comprises focusing optics 28, including lenses 19, 20, and a CCD (Charge coupled device) detector array 21. A linear array is sufficient for the purposes of the invention. The lens 20 diverges the return object beam and spreads it over the entire width of the CCD detector array 21.

The reference beam passes through optical fiber 11 and splitter/combiner 12 to optical path length adjusting unit 29 for varying the optical path length. This comprises a pair of movable mirrors 23, disposed at 45° angles, which can be moved back and forth in the direction of arrow A. Light emerging from optical fiber 24 carrying the reference beam from the splitter/combiner 12 is directed by lens 25 onto one of the pair of mirrors 23, which direct it back through lens 26 into optical fiber 27. Displacement of the mirrors 23 in the direction of the arrow A changes the optical path length of the reference beam, which is then returned through polarization controller 18 to focusing optics 28.

The lens 19 spreads the reference beam over the entire width of the CCD detector array 21, such that the reference beam overlaps the object beam over the full extent of the individual pixels $P_0 \ldots P_N$ of the detector array 21. The reference beam and object beam thus interfere at each pixel location $P_n$, and a signal is produced from the modulation imposed on the object beam, as described in U.S. Pat. No. 5,975,697. The preferred method of modulating the object beam is to rely on the modulation effect caused by scanning the beam across the target with a galvo-scanner as described in more detail in this patent.

As is well known in OCT, a signal will be obtained only from the depth within the target where the optical path difference lies within the coherence length. The depth resolution of the imaging equipment thus depends on the coherence length of the source. At any given pixel $P_n$, the optical path difference between the object and reference beams will depend on the position of the displaceable mirrors 23 and on the lateral position of the pixel $P_n$ as a result of the different paths from lens 19, 20 to any particular pixel $P_n$ in the array. In FIG. 1, the two extreme pixels $P_0$ and $P_N$ are shown. It will be seen that the path lengths from the two lenses 19, 20 to pixel $P_1$, for example, are different.

The $Z_0$ or base plane, which in this case is the median plane, is set by the position of the displaceable mirrors 23, and this typically corresponds to the middle pixel in the linear array where the path length from the two lenses 19, 20 is the same. Then for each point on the target, different pixels obtain information from an image plane at a depth $Z_0 \pm \delta Z$, where $\delta Z$ depends on the path difference between the two paths from the lenses 19, 20 to the pixel $P_n$ in question.

It will thus be seen that the data set from a complete array provides image information for each point on the target at depth positions varying between $Z_0 \pm \Delta Z$, where in this case $\Delta Z$ corresponds to the optical path difference at the extreme ends of the CCD array.

Each point on a scanning line will in turn produce its own set of data corresponding to the image information at depth positions $Z_0 \pm \Delta Z$. Thus, a single transverse scan contains a number of sets of data corresponding to the number image points on the target, which is determined by the resolution of the system, namely the number of times during a scan that a data set is stored. These sets of data contain image information corresponding to a transverse section at depths positions $Z_0 \pm \Delta Z$. Subsequent scanning lines contain similar information for a different Y coordinate. Consequently, multiple transverse scans contain all the information necessary to obtain a three dimensional image over a volume determined by the X-Y coordinates in the en-face plane and the distance $Z_0 \pm \Delta Z$ determined by the length of the CCD array and the geometry of the focusing optics.

It will be understood that although the transverse scanning has been described in the X-direction, which coordinate is scanned transversely in the X-Y plane is immaterial. It is equally possible to scan vertically in the Y direction, and translate the scanning line in the X direction after each vertical scan.

The processing is performed in computer 40, which may be a personal computer with memory 41, for example, a hard drive, and a display device 42, such as an LCD display. The computer 40 can receive the data from the detector 21 over a parallel cable to a suitable interface card inserted into the motherboard, or alternatively over a USB link. The images generated by the computer 40 can be displayed on the display device 42, for example, as en-face images at different depths. Alternatively, once the three-dimensional image information has been stored in memory 41, the computer can generate longitudinal sections (B-scans) or any other scans that may be desired.

Figure 2:
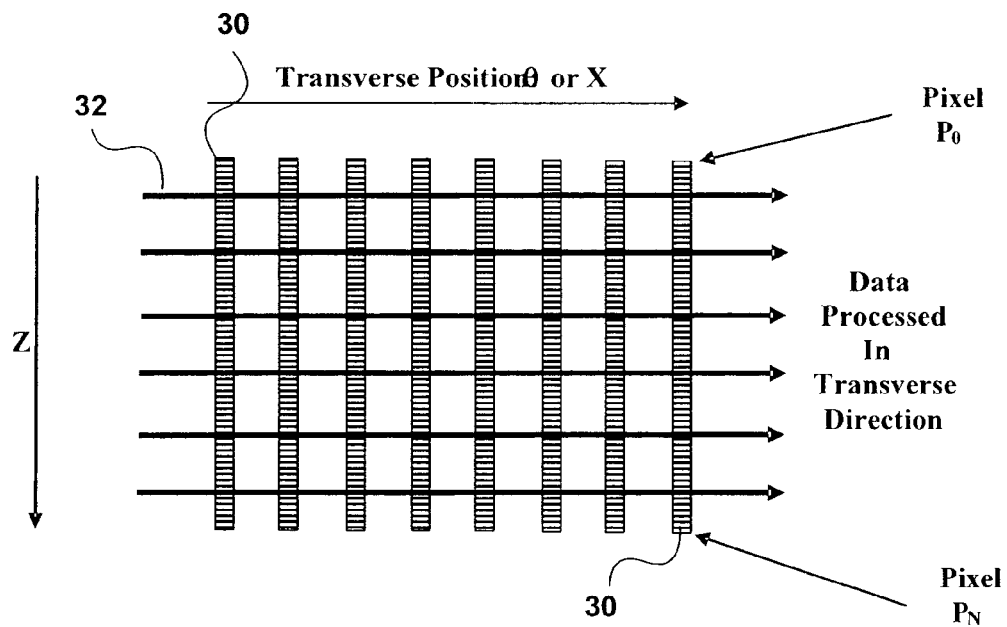
FIG. 2 is a diagram showing how the OCT data is processed.
Figure 3:
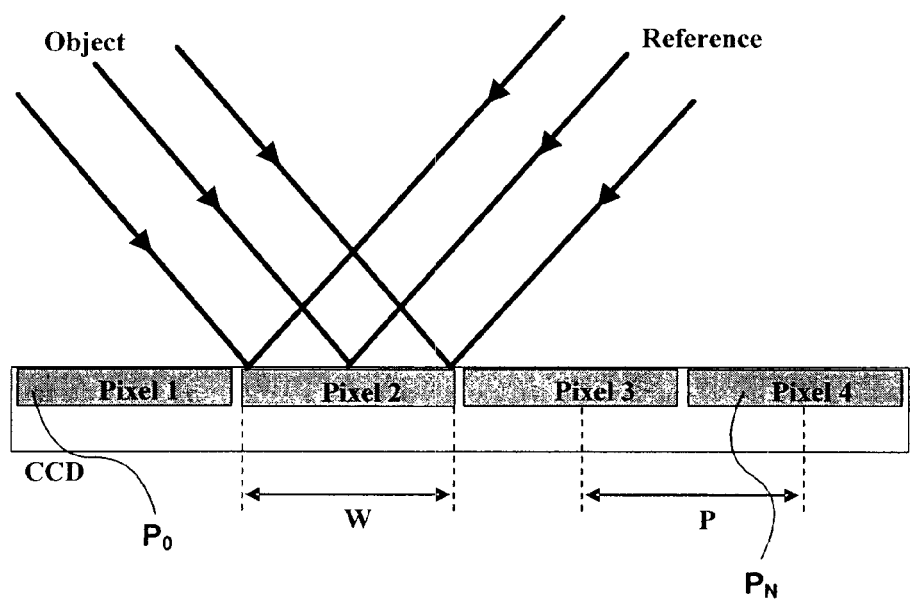
FIG. 3 is a detailed illustrated showing the combination of the object and reference beams at a pixel of the detector.

FIG. 2 shows the scanning scheme. In FIG. 2, each vertical line 30 represents an array of pixels $P_0 \ldots P_N$ of the CCD array. The horizontal lines 32 represent the transverse scans. For each transverse point a full subset of data is captured, represented by the vertical lines, which represents the reflectivity information in the Z-direction at a series of points extending over the range $Z_0 \pm \Delta Z$ because each pixel corresponds to a different optical path difference.

In order to create an image, a line of data corresponding to a point in the X-Y plane is processed in the computer 40 to generate image information for a series of points $Z_0 \pm \Delta Z$ in the Z-direction. This process is repeated for each line of data to generate a multiple sets of points in the Z-direction corresponding to each X-position in the transverse scan, assuming a scan in the X-direction. These image points permit the creation of a sectional image in the Z-direction along the scanning line. By repeating the process for different scanning lines, when the image is scanner as a raster, a complete three dimensional image of the retina can be constructed.

It will be noted that according to the invention, data for all the points extending over the depth range $Z_0 \pm \Delta Z$ is captured in parallel. It is thus only necessary to perform one raster scan in the X-Y direction to construct a complete three-dimensional image instead of performing multiple scans at different depth ranges.

We claim:

1. A method of generating images in an OCT apparatus from a target in a coordinate system wherein depth is defined by a Z direction and an en-face image plane lies in an X-Y plane, wherein an object light beam is returned from the target and interferes with a reference light beam, and wherein image information is obtained from a depth Zn in the target, with a resolution that depends on the coherence length of the light, by varying the optical path difference between the object and reference beams, comprising:
   transversely scanning the target with the object beam over a plurality of image points in at least one scanning line in the X-Y plane, wherein the number of image points is defined by the resolution of the apparatus;
   spreading the reference beam and the object beam returned from each individual image point on the target during each transverse scan onto a linear array of detector elements so that for each individual image point the reference beam and object beam interfere simultaneously over the array of detector elements and the optical path difference varies across the array such that the optical path difference is different at each detector element in the array;
   for each said individual image point storing a subset of data points obtained from each detector element of the array;
   processing said subsets of data points obtained from each detector element of the array to derive image information extending over a range of depths in the target for each said individual image point; and
   processing a set of said data points comprising a plurality of said subsets, wherein each subset is obtained from each image point in a scanning line to produce sectional image information along a line in the X-Y plane extending in the z-direction into said target.

2. A method as claimed in claim 1, comprising processing a superset of said data points, said superset comprising a plurality of said sets, wherein each set corresponds to a different scanning line, to produce three dimensional image information about the target.

3. A method as claimed in claim 1, further adjusting the path length of the reference beam to set a base depth range $Z_0$ in said target such that the different detector elements in said array correspond to depths $Z_0 \pm \delta Z$, where $\delta Z$ corresponds to the additional path difference between said object beam and said reference beam introduced by the displacement of the detector elements from the detector element corresponding to depth $Z_0$.

4. A method as claimed in claim 3, where the path length is adjusted with a displaceable mirror inserted in the reference beam.

5. A method as claimed in claim 1, wherein said object beam and said reference beam are guided in optical fibers, light emerging from said fibers is diverged by interface optics to extend over said array of detector elements.

6. A method as claimed in claim 5, wherein said array of detector elements is a charge coupled device.

7. A method as claimed in claim 1, further comprising controlling the polarization of light in said object and reference beams.

8. A method as claimed in claim 1, wherein said target is scanned in a raster fashion.

9. An OCT apparatus for generating images from a target in a coordinate system wherein depth is defined by a Z direction and an en-face image plane lies in an X-Y plane, wherein an object light beam is returned from the target and interferes with a reference light beam, and wherein image information is obtained from a depth Zn in the target, with a resolution that depends on the coherence length of the light, by varying the optical path difference between the object beam returned from the target and the reference beam comprising:
   a scanner for transversely scanning the target with the object beam over a plurality of image points in at least one scanning line in the X-Y plane, wherein the number of image points is defined by the resolution of the apparatus;
   a linear array of detector elements;
   interface optics for spreading the reference beam and the object beam returned from each individual image point on the target during each transverse scan onto the array of detector elements so that for each individual image point the reference beam and object beam interfere simultaneously over the linear array of detector elements and the optical path difference between the reference beam and the object beam varies across the array such that the optical path difference is different for each detector element in the array;
   a memory for storing a subset of data points corresponding to each said individual image point and obtained from each detector element of the array; and
   a processor configured to process said subsets of data points obtained from each detector element of the array to derive image information extending over a range of depths in the target for each said individual image point, and to process a set of said data points comprising a plurality of said subsets, wherein each subset is obtained from each image point in a scanning line to produce sectional image information along a line in the X-Y plane extending in the z-direction into said target; and a display device for displaying said image information.

10. An OCT apparatus as claimed in claim 9, wherein said processor is configured to process a superset of said data points, said superset comprising a plurality of said sets, wherein each set corresponds to a different scanning line, to produce three dimensional image information about the target.

11. An OCT apparatus as claimed in claim 9, further comprising means for adjusting the path length of the reference beam to set a base depth range $Z_0$ in said target such that the different detector elements in said array correspond to depths $Z_0 \pm \delta Z$, where $\delta Z$ corresponds to the additional path difference between said object beam and said reference beam introduced by the displacement of the detector elements from the detector element corresponding to depth $Z_0$.

12. An OCT apparatus as claimed in claim 11, wherein said adjusting means comprises a displaceable mirror inserted in the reference beam.

13. An OCT apparatus as claimed in claim 9, further comprising optical fibers for guiding said object beam and said reference beam, and interface optics for diverging light emerging from said fibers onto said array of detector elements.

14. An OCT apparatus as claimed in claim 13, wherein said array of detector elements is a charge coupled device.

15. An OCT apparatus as claimed in claim 9, further comprising polarizers for controlling the polarization of light in said object and reference beams.

16. An OCT apparatus as claimed in claim 9, wherein said scanner is a galvo scanner configured to scan said target in a raster fashion, with the rate of scanning transversely being fast relative to the rate of scanning vertically.

\* \* \* \* \*